United States Patent
Wittnebel et al.

(10) Patent No.: US 11,376,159 B2
(45) Date of Patent: Jul. 5, 2022

(54) SYSTEM AND METHOD FOR AUTOMATED POSITION MAINTENANCE OF AN OPHTHALMIC SURGERY CONE

(71) Applicant: Novartis AG, Basel (CH)

(72) Inventors: Michael Wittnebel, Hirschaid (DE); Mario Abraham, Burgthann (DE)

(73) Assignee: Alcon Inc., Fribourg (CH)

( * ) Notice: Subject to any disclaimer, the term of this patent is extended or adjusted under 35 U.S.C. 154(b) by 345 days.

(21) Appl. No.: 16/334,594

(22) PCT Filed: Oct. 28, 2016

(86) PCT No.: PCT/IB2016/056537
§ 371 (c)(1),
(2) Date: Mar. 19, 2019

(87) PCT Pub. No.: WO2018/078425
PCT Pub. Date: May 3, 2018

(65) Prior Publication Data
US 2020/0246183 A1 Aug. 6, 2020

(51) Int. Cl.
*A61F 9/009* (2006.01)
*A61F 9/008* (2006.01)
*A61F 9/00* (2006.01)

(52) U.S. Cl.
CPC .......... *A61F 9/009* (2013.01); *A61F 9/00825* (2013.01); *A61F 2009/0052* (2013.01);
(Continued)

(58) Field of Classification Search
CPC ...... A61F 9/009; A61F 9/008; A61F 9/00802; A61F 9/00821; A61F 9/00825; A61F 2009/00844; A61F 2009/00846; A61F 2009/00851; A61F 2009/00861; A61F 2009/00863; A61F 2009/0087;
(Continued)

(56) References Cited

U.S. PATENT DOCUMENTS 9,844,463 B2 * 12/2017 Watanabe ........... A61F 9/00829
9,918,873 B2 * 3/2018 Woodley ............. A61F 9/00827
(Continued)

FOREIGN PATENT DOCUMENTS

| CN | 101237811 A | 8/2008 | |
| EP | 2913036 A1 * | 9/2015 | ......... A61F 9/00825 |

(Continued)

*Primary Examiner* — Ahmed M Farah (57) ABSTRACT

The present disclosure provides a system and method for maintaining the position of a suction cone on an eye during laser ophthalmic surgery that includes determining a distance and direction the suction cone or a support must be adjusted to maintain the position of the suction cone within an optimal working range, based on a detected position of the suction cone. The disclosure further provides a method for maintaining the position of a suction cone by determining a distance and direction the suction cone or a support must be adjusted to maintain the position of the suction cone within an optimal working range, based on a detected position of the suction cone. In the system and the method, a control signal is generated to adjust the position of the suction cone and/or the support to maintain the suction cone within the optimal working range.

20 Claims, 4 Drawing Sheets

(52) U.S. Cl.
CPC ............ *A61F 2009/00846* (2013.01); *A61F 2009/00872* (2013.01); *A61F 2009/00887* (2013.01)

(58) Field of Classification Search
CPC .. A61F 2009/00872; A61F 2009/00885; A61F 2009/00887; A61F 2009/00893; A61F 2009/00895; A61F 2009/00842
USPC ..................................... 606/4–6, 10–12, 166
See application file for complete search history.

(56) References Cited

U.S. PATENT DOCUMENTS

| | | | |
|---|---|---|---|
| 10,292,863 B2 * | 5/2019 | Gooding | A61F 9/009 |
| 10,335,315 B2 * | 7/2019 | Goldshleger | A61F 9/009 |
| 10,420,677 B2 * | 9/2019 | Wittnebel | A61F 9/00825 |
| 10,980,672 B2 * | 4/2021 | Wittnebel | A61F 9/009 |
| 11,033,185 B2 * | 6/2021 | Wittnebel | G06T 7/0012 |
| 2008/0278687 A1 * | 11/2008 | Somani | A61B 3/0083 351/208 |
| 2013/0041354 A1 * | 2/2013 | Brownell | A61F 9/00836 606/4 |
| 2014/0114297 A1 * | 4/2014 | Woodley | A61B 5/0036 606/6 |
| 2014/0128852 A1 | 5/2014 | Gooding et al. | |
| 2019/0231594 A1 * | 8/2019 | Abraham | G06T 7/70 |
| 2019/0247233 A1 * | 8/2019 | Schmid | A61F 9/00836 |

FOREIGN PATENT DOCUMENTS

| | | |
|---|---|---|
| EP | 2913036 A1 | 9/2015 |
| JP | 2015163092 A2 | 9/2015 |
| WO | 2016061552 A1 | 4/2016 |

* cited by examiner

FIGURE 3

SYSTEM AND METHOD FOR AUTOMATED POSITION MAINTENANCE OF AN OPHTHALMIC SURGERY CONE

TECHNICAL FIELD

The present disclosure relates to ophthalmic surgery and surgical equipment, and more specifically, to systems and methods for maintaining the position of a suction cone on an eye during laser ophthalmic surgery.

BACKGROUND

Ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is surgery performed on the eye or any part of the eye. Ophthalmic surgery is regularly performed to repair retinal defects, repair eye muscles, remove cataracts or cancer, or to restore or improve vision. Refractive eye surgery, for example, is a type of ophthalmic surgery used to improve the refractive state of the eye for the purpose of decreasing or eliminating dependency on glasses or contact lenses. Refractive surgery procedures may include surgically remodeling the cornea and/or cataract surgery, either of which may be performed by lasers.

In various ophthalmic surgical procedures, a laser uses photodisruption to create incisions. When performing ophthalmic surgery with lasers, a surgical procedure typically includes docking, imaging, analysis, and laser treatment. During docking, a patient's eye is docked to a suction cone in order to provide pressure to flatten the patient's cornea (known as applanation) and hold it in position for the laser treatment. Docking is a sensitive process, and proper placement of the suction cone is important for successful ophthalmic surgery. However, correct placement of the suction cone is currently typically guided through visual inspection by the user, relying on experience and perception Before docking and throughout the procedure, a patient is typically positioned on a support.

SUMMARY

The present disclosure provides a system for maintaining the position of a suction cone on an eye during laser ophthalmic surgery. The system includes a suction cone, a first control device operable to adjust a position of the suction cone, a measuring device operable to detect a detectable position of the suction cone and generate data relating to the detectable position, a support, a second control device operable to adjust a position of the support, a display, and a processor operable to receive data from the measuring device relating to the detectable position, determine whether the detectable position of the suction cone is within an optimal working range, determine a distance and direction the suction cone or support must be adjusted to maintain the detectable position within an optimal working range, determine whether only the suction cone can be adjusted to maintain the detectable position within an optimal working range, and if not, whether the support may be adjusted alone or in addition to the suction cone, generate a control signal operable to adjust the position of the suction cone, if only the suction cone may be adjusted, generate a control signal operable to adjust a position of the support, if the support may be adjusted, generate a first control signal operable to adjust the position of the suction cone and a second control signal operable to adjust a position of the support, if the support, if neither the suction cone or the support may be adjusted alone, transmit the control signal operable to adjust the detectable position to the first control device to adjust the position of the suction cone, and/or transmit the control signal operable to adjust the position of the support to the second control device to adjust the position of the support, to maintain the detectable position of the suction cone within the optimal working range, process the data relating to the detectable position to generate a pictorial representation of the suction cone and the eye, and transmit the pictorial representation to the display.

In additional embodiments, which may be combined with one another unless clearly exclusive: the measuring device is operable to detect a detectable position of the suction cone by using light barriers, switches, an eye camera, multiple eye cameras, or an eye tracking system; the support is a couch or a bed; the system further comprises a device for manual confirmation of an adjustment, the device operable to input a confirmation; the device for manual confirmation of an adjustment is a button, a switch, a key, a joystick, a receiver for a spoken confirmation, or any combination thereof; and the processor is further configured to require receipt of a manual confirmation input before either generating a control signal or transmitting a control signal already generated.

The present disclosure further provides a method for maintaining the position of a suction cone on an eye during laser ophthalmic surgery. The method includes receiving data from a measuring device relating to a detectable position of a suction cone, determining whether the detectable position of the suction cone is within an optimal working range, determining a distance and direction the suction cone or a support must be adjusted to maintain the detectable position within an optimal working range, determining whether only the suction cone can be adjusted to maintain the detectable position within the optimal working range, and if not, whether the support may be adjusted alone or in addition to the suction cone, generating a control signal operable to adjust the detectable position, if only the suction cone can be adjusted to maintain the detectable position within the optimal working range, generating a control signal operable to adjust a position of the support, if only adjusting the suction cone is unable to maintain the detectable position within the optimal working range, transmitting the control signal operable to adjust the detectable position to the first control device, to adjust the position of the suction cone, or transmit the control signal operable to adjust the position of the support to the second control device, to adjust the position of the support, so that the detectable position of the suction cone is maintained within the optimal working range, processing the data relating to the detectable position to generate a pictorial representation of the suction cone and the eye, and transmitting the pictorial representation to a display.

In additional embodiments, which may be combined with one another unless clearly exclusive: the measuring device is operable to detect a detectable position of the suction cone by using light barriers, switches, an eye camera, multiple eye cameras, or an eye tracking system; the support is a couch or a bed; the method further comprises a device for manual confirmation of an adjustment, the device operable to input a confirmation; the device for manual confirmation of an adjustment is a button, a switch, a key or a joystick, or any combination thereof; the method further comprises determining whether manual confirmation is required to perform an adjustment of the suction cone or the support, the method further comprising determining whether manual confirmation has been input, and the method further comprising requiring receipt of a manual confirmation input before a control signal is generated or a control signal already generated is transmitted.

The above systems may be used with the above methods and vice versa. In addition, any system described herein may be used with any method described herein and vice versa.

BRIEF DESCRIPTION OF THE DRAWINGS

For a more complete understanding of the present invention and its features and advantages, reference is now made to the following description, taken in conjunction with the accompanying drawings, which are not to scale, in which like numerals refer to like features, and in which.

DETAILED DESCRIPTION

In the following description, details are set forth by way of example to facilitate discussion of the disclosed subject matter. It should be apparent to a person of ordinary skill in the field, however, that the disclosed embodiments are exemplary and not exhaustive of all possible embodiments.

The present disclosure provides systems and methods for maintaining the position of a suction cone on an eye during laser ophthalmic surgery. At the beginning of an ophthalmic surgical procedure, a patient is typically placed on a support facing upward. The support may be, for example, a couch or a bed. Before laser treatment, a suction ring is positioned on the eye and held in place and in contact with the eye by a first vacuum. A suction cone is lowered to and docked to the suction ring and held in place by a second vacuum. The suction cone should be docked within an "optimal working range," which may be defined as a range in the Z-direction that is preferable or necessary for the suction cone to be within, where the vacuum pressure on the eye is within a safe range and the suction between the eye, the docked suction ring, and the docked suction cone is stable and no leakage is present. The suction cone should be kept within this optimal working range throughout the surgical procedure. Any movement that results in the suction cone leaving the optimal working range may cause the vacuum on the eye to be lost. Generally, if the vacuum is lost during an operation, surgery must be paused, the user must re-perform the docking procedure, and the vacuum on the eye must be re-established before surgery may continue. This is a time-intensive and work-intensive solution that increases the risk of discomfort, bruising, inflammation, and other potentially dangerous side effects to the patient.

The X and Y-directions are in a plane roughly perpendicular to the apex of the cornea. The Z direction is in a plane roughly perpendicular to the plane of the X and Y-directions. In the present disclosure, "lower," "down" and "downwards" in the Z-direction refer to movement or a position closer to the patient's eye. "Higher," "up" and "upwards" in the Z-direction refer to movement or a position further away from the patient's eye.

In other systems, vacuum pressure is monitored wherein a reduction in pressure may indicate a change in position of the eye, the suction ring, or the suction cone. In response, the user must manually correct the position of the patient on the support, manually correct the position of the suction ring, or manually correct the position of the suction cone, based on visual inspection, experience and perception. Significantly, the effect of leakage on vacuum pressure is rapid. Thus, upon detection of any drop in pressure, the vacuum is often already lost and the eye must be re-docked. Because a continuous drop in vacuum pressure is improbable and the user is often unable to correct the leakage before it is necessary to re-dock the eye, detection of change in vacuum pressure is ineffective as a regulating parameter.

Figure 1:
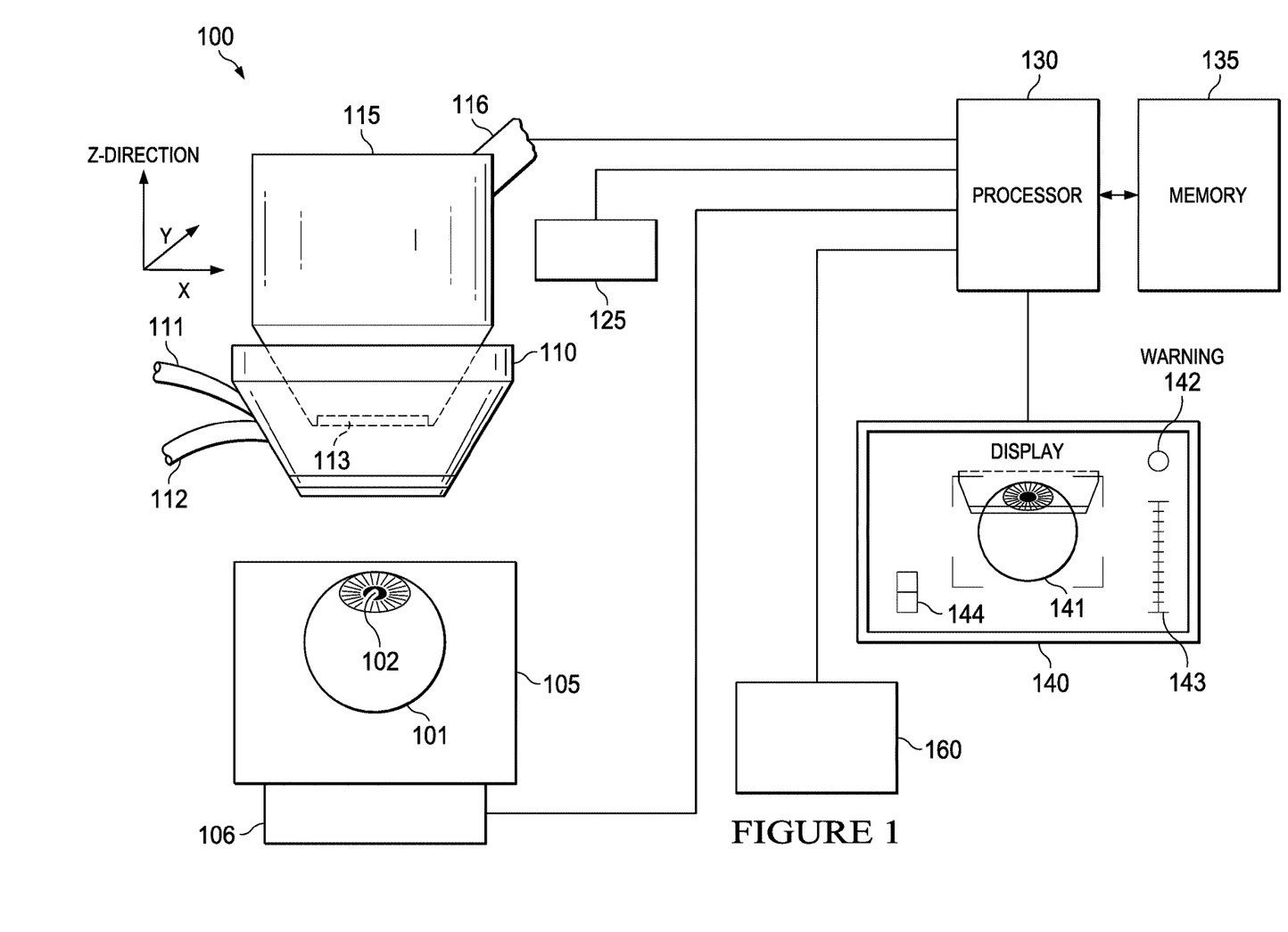
FIG. 1 is a schematic representation of elements of a system for maintaining the position of a suction cone on an eye during laser ophthalmic surgery.

Referring now to the figures, FIG. 1 is a schematic representation of elements of a system 100 for maintaining the position of a suction cone on an eye during laser ophthalmic surgery. As shown, system 100 includes a support 105, upon which a patient is placed facing upward, the support connected to a second control device 106. The system further provides suction ring 110, attached to first vacuum 111 and second vacuum 112, and suction cone 115, which is connected to first control device 116 and which includes lens 113. To detect a detectable position of the suction cone, the system provides measuring device 125, operable to detect and generate data relating to a detectable position of the suction cone, and transmit the data to processor 130. Processor 130 is connected through a cable-connected or wireless connection to at least memory 135, first control device 116, second control device 106, measuring device 125, display 140, and device for manual confirmation of an adjustment 160. Processor 130 is operable to process data relating to the detectable position, determine the distance and direction the suction cone or support must be adjusted so that the detectable position of the suction cone is within an optimal working range, generate a control signal operable to adjust the position of the suction cone or support, and transmit the control signal to either first control device 116 to adjust the suction cone, or second control device 106 to adjust the support. Processor 130 is further operable to generate a pictorial representation indicating the detectable position of the suction cone and transmit the pictorial representation to display 140 for presentation to a user.

At the beginning of an ophthalmic surgical procedure, a patient is placed on support 105 facing upward. Support 105 is connected to second control device 106, which is operable to adjust the position of the support at least in the Z-direction. Second control device 106 may be further operable to adjust the position of the support in the X and Y-directions. Suction ring 110 may then be positioned on the eye manually or via a third control device. If positioned manually, the suction ring may be handled directly or with a handling device, such as forceps. If positioned via a third control device, the suction ring may be connected to an electronically controlled assembly. The electronically controlled assembly may be used to adjust the position of the suction ring instead of manually handling the suction ring. After suction ring 110 is positioned on the eye, suction cone 115 may be docked to the suction ring. Suction cone 115 is connected to first control device 116, which is operable to adjust the position of the suction cone in the Z-direction. First control device 116 may be further operable to adjust the position of the suction cone in the X and Y-directions.

System 100 further provides a measuring device 125 operable to detect a detectable position of the suction cone in the Z-direction, and may be further operable to detect a detectable position of the suction cone in the X and Y-directions. Measuring device 125 may be a cable-connected or wireless device, and may be operable to detect a detectable position of the suction cone by using, for example, light barriers, switches, an eye camera, multiple eye cameras, an eye tracking system, or any combination thereof. Measuring device 125 is operable to generate data relating to the detectable position and transmit the data generated to processor 130.

Processor 130, connected to memory 135, is operable to receive data from the measuring device relating to the detectable position, determine whether the detectable position of the suction cone is within an optimal working range, and determine a distance and direction the suction cone or support must be adjusted to maintain the detectable position within an optimal working range. Processor 130 may also determine whether only the suction cone can be adjusted to maintain the detectable position within an optimal working range, and if not, whether the support may be adjusted alone or in addition to the suction cone. By maintaining the detectable position of the suction cone within the optimal working range, system 100 maintains a stable vacuum pressure between the eye, the docked suction ring, and the docked suction cone with no leakage.

If only the suction cone may be adjusted to maintain the detectable position within the optimal working range, then processor 130 may generate a control signal operable to adjust the suction cone and transmit the control signal to first control device 116. If the support must be adjusted to maintain the detectable position within the optimal working range, then processor 130 may generate a single control signal operable to adjust the support and transmit the control signal to second control device 106. If the support must be adjusted in combination with the suction cone, then processor 130 may generate and transmit a first control signal to first control device 116 and a second control signal to second control device 106. If neither the support alone, or in addition to the suction cone may be adjusted to maintain the suction cone within the optimal working range, then processor 130 may generate a warning, the warning indicating that automated adjustment is unavailable. Processor 130 may then transmit this warning to display 140 to be presented to a user. Such warning, for example, may be in the form of a colored light, a blinking light, a flashing light, a sound, an alarm, a whistle, a graphic, or any other signal operable to indicate to the user that automated adjustment is not available. The warning may be presented to the user in real time, preferably as soon as it is determined that automated adjustment is unavailable. Real time may mean in less than half a second, in less than one second, or otherwise in less than the normal reaction time of a user based on visual information.

Processor 130 is further operable to process the data received from measuring device 125 relating to the detectable position, to generate a pictorial representation 141 of the suction cone and the eye. Processor 130 may also transmit the pictorial representation to display 140. Display 140 may include multiple displays and may be a screen, a heads-up display, or a combination. As shown in FIG. 1, pictorial representation 141 may also include, for example, a warning light or graphic 142, a graphic indicating the detectable position in the Z-direction as a scale 143, other graphics indicating the detectable position in the X and Y-directions, or graphic indicating manual confirmation of an adjustment is required 144. Any of the graphics may be superimposed or presented on any part of pictorial representation 141. One or more pictorial representations may be presented on display 141, for example, a pictorial representation of the detectable position when the eye is first docked and a pictorial representation of the detectable position as detected during the procedure.

Processor 130 may further be connected to device for manual confirmation 160, and processor 130 may further be configured to receive and process data or an input from device for manual confirmation 160. Device for manual confirmation 160 of an adjustment may be a button, a switch, a key, a joystick, or any device operable to input a confirmation, which includes devices for receiving a spoken confirmation. If processor 130 is configured to receive and process data or an input from device for manual confirmation 160, then processor 130 may determine whether data or an input indicating a manual confirmation has been received, and generate a control signal for the first control device and/or the second control device. System 100 may be configured to require manual confirmation to either generate a control signal or transmit a control signal that has already been generated. If processor 130 is configured to require manual confirmation, and manual confirmation has not been received, processor 130 may proceed to a standby mode prior to either generating or transmitting a control signal. Alternatively, processor 130 may be configured not to require any manual confirmation, or to automatically perform a manual confirmation for a period of time without receiving an actual manual confirmation from a user.

Processor 130 may comprise, for example a microprocessor, microcontroller, digital signal processor (DSP), application specific integrated circuit (ASIC), or any other digital or analog circuitry configured to interpret and/or execute program instructions and/or process data. In some embodiments, processor 130 may interpret and/or execute program instructions and/or process data stored in a memory. The memory may be configured in part or whole as application memory, system memory, or both. The memory may include any system, device, or apparatus configured to hold and/or house one or more memory modules. Each memory module may include any system, device or apparatus configured to retain program instructions and/or data for a period of time (e.g., computer-readable media). The various servers, electronic devices, or other machines described may contain one or more similar such processors or memories for storing and executing program instructions for carrying out the functionality of the associated machine.

Figure 2A:
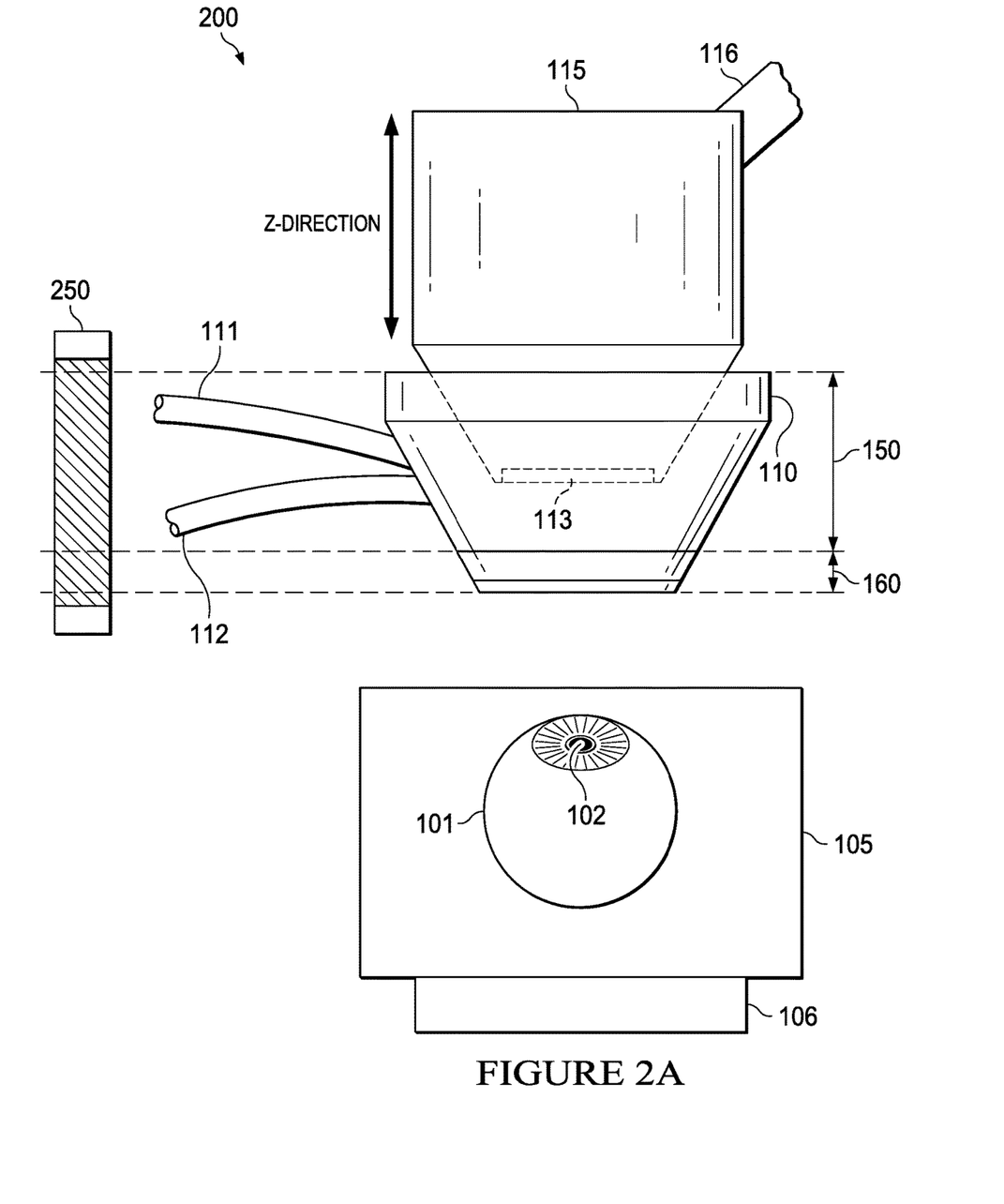
FIG. 2A is a schematic representation of a system for maintaining the position of a suction cone on an eye, in which the system is in a state before docking and the suction cone is not within an optimal working range.

FIG. 2A is a schematic representation of a system for maintaining the position of a suction cone on an eye, in which the system is in a state before docking and the suction cone is not within an optimal working range. As shown, a typical docking apparatus 200 includes a suction ring 110 and a suction cone 115, which are vacuum suctioned to a patient's eye 101 via first vacuum 111 and second vacuum 112. Suction cone 115 may include a lens 113. The first and second vacuums are operable to cause the suction ring and suction cone to maintain contact with the eye within an optimal working range, throughout the surgical procedure.

In FIG. 2A, suction cone 115 is connected to first control device 116, which is operable to adjust the position of the suction cone in the Z-direction. First control device 116 may be further operable to adjust the position of the suction cone in the X and Y-directions, defined as a plane roughly perpendicular to the apex of the cornea. Suction cone 115 may be connected to first control device 116 through a cable-connected or wireless connection. Similarly, support 105, which a patient is placed upon during a surgical procedure, is connected to a second control device 106, which is operable to adjust the position of the support in the Z-direction. Second control device 106, may be further operable to adjust the position of the support in the X and Y-directions. Support 105 may be connected to second control device 106 through a cable-connected or wireless connection. Measuring device 250 is operable to detect a detectable position of the suction cone in the Z-direction, and may be further operable to detect a detectable position in the X and Y-directions. Measuring device 250 is further operable to generate and transmit data relating to the detectable position to a processor, such that the processor may determine whether the detectable position is within optimal working range 150. As an example, a sub-optimal range 160 is shown below the optimal working range. If the detectable position of the suction cone is determined to be within sub-optimal range 160, then automated adjustment may be performed in accordance with the disclosed systems and methods.

System 200 as shown in FIG. 2A is in a state before docking, as indicated by a lack of contact between the patient's eye 101 and the suction cone or suction ring. During docking, measuring device 250 may be first used to detect whether the eye is within optimal working range 150. Once docking is complete and the surgical procedure begins, measuring device 250 may be used to subsequently detect any eye movement that causes the detectable position of the suction cone to move within or outside of optimal working range 150. Sub-optimal working range 160 may be defined as any range outside of the boundaries of the optimal working range, and may be above or below the optimal working range. The user may define multiple sub-optimal working ranges and such sub-optimal working ranges may overlap to any degree in order to provide the user with a more nuanced indication of the extent to which the suction cone is outside of the nearest optimal working range boundary.

Figure 2B:
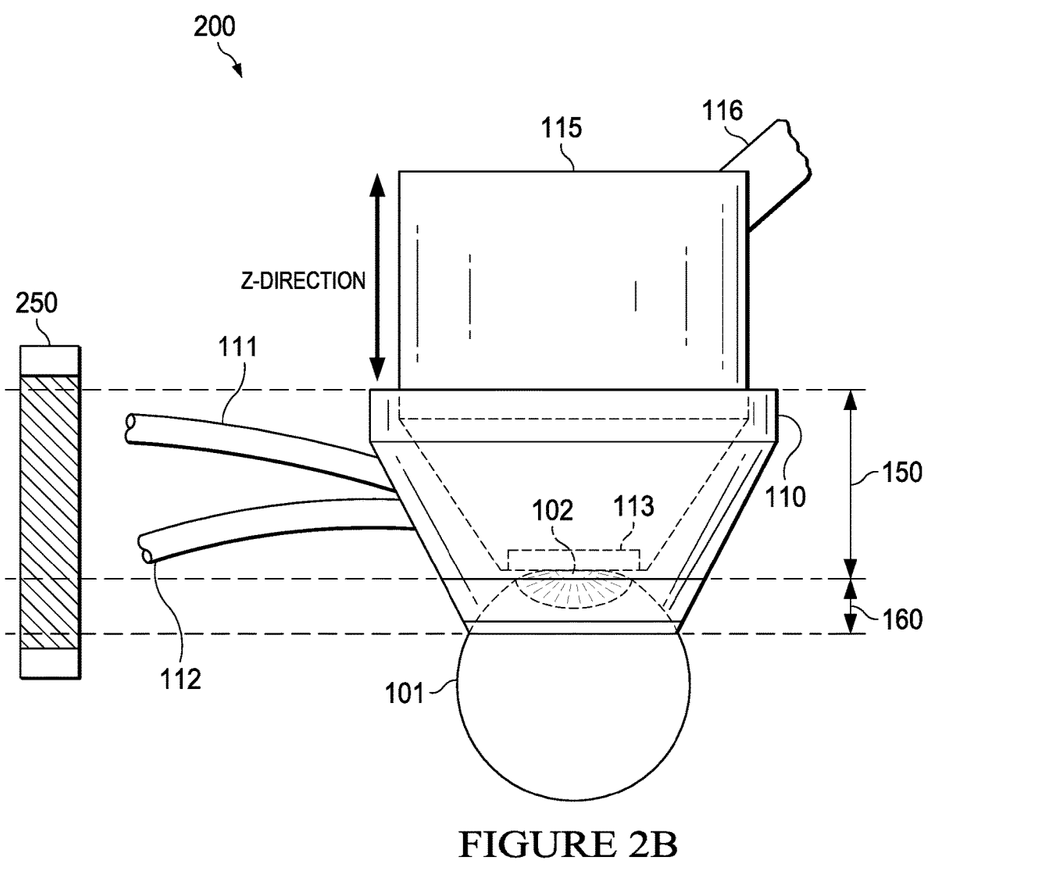
FIG. 2B is a schematic representation of a system for maintaining the position of a suction cone on an eye, in which the system is in a docked state and the suction cone is within an optimal working range.

FIG. 2B is a schematic representation of a system for maintaining the position of a suction cone on an eye, in which the system is in a docked state and the suction cone is within an optimal working range. As shown in FIG. 2B, suction ring 110 is in contact with eye 101 and suction cone 115 is docked to the suction ring such that first vacuum 111 and second vacuum 112 may provide adequate suction for proper applanation. In this example, measuring device 250 may detect a detectable position of suction cone 115 and generate data relating to the detectable position. Such data may include data relating to the detectable position in the Z-direction and also in the X and Y-directions, defined as a plane roughly perpendicular to the apex of the cornea. When it is determined that the detectable position of the suction cone is within optimal working range 150, the user may begin the surgical procedure.

In contrast to FIG. 2A, automated adjustment of the suction cone is not necessary, as shown in FIG. 2B, because the suction cone is within optimal working range 150. In the optimal working range, lens 113 is in contact with the eye 101 at a position in the Z-direction operable to cause applanation. From this docked position in the optimal working range, the user may begin the surgical procedure. However, throughout the procedure, the patient may move, causing the detectable position of the suction cone to change. Such movement may cause the detectable position to breach the upper or lower boundary of the optimal working range. For example, if the detectable position approaches the lower boundary of the optimal working range, thus approaching the top of sub-optimal range 160, then measuring device 250 may detect the change in the Z-direction and generate data relating to the new detectable position. Such data may be processed to determine the distance and direction the suction cone must be adjusted to maintain the detectable position within optimal working range 150, and a control signal operable to adjust the position of the suction cone, the support, or the support in addition to the suction cone may be generated. As an example, if the detectable position may be maintained within the optimal working range by only moving the suction cone, then a control signal may be generated and transmitted to first control device 116. First control device 116 may then adjust the position of the suction cone in accordance with the distance and direction determined to maintain the detectable position within the optimal working range.

Figure 3:
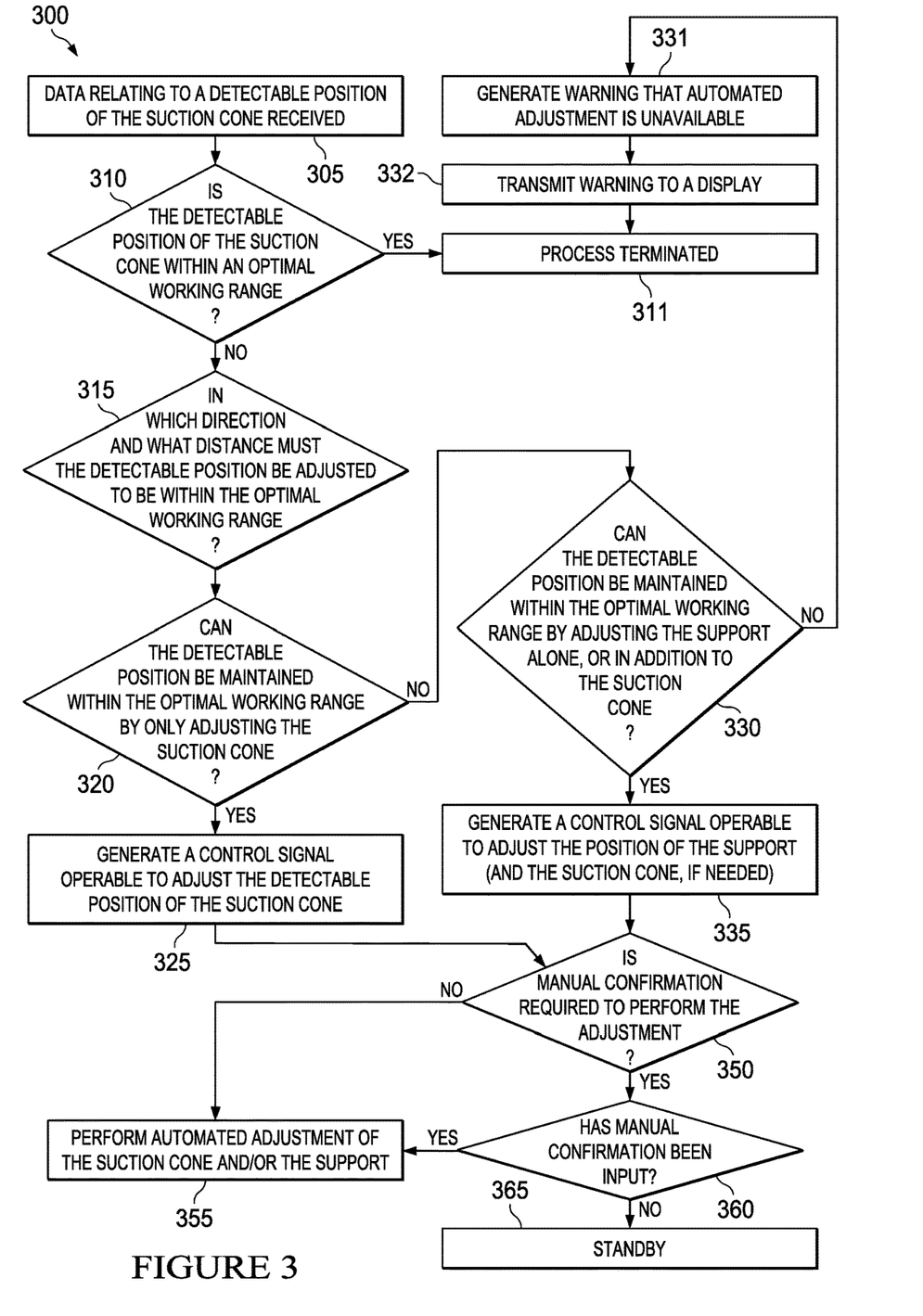
FIG. 3 is a flow chart of a method for maintaining the position of a suction cone on an eye during laser ophthalmic surgery.

FIG. 3 is a flow chart of a method for maintaining the position of a suction cone on an eye in laser ophthalmic surgery. At step 305, data relating to a detectable position of a suction cone is received. Such data detected and transmitted may include data relating to the position of the suction cone in the Z-direction. Such data may further include the position of the suction cone in the X and Y-directions.

At step 310, whether the detectable position of the suction cone is within an optimal working range may be determined. If the detectable position of the suction cone is within the optimal working range, then at step 311, the process terminates or otherwise does not cause the detectable position to be changed because no automated adjustment is required to maintain the detectable position within the optimal working range. In contrast, if the detectable position of the suction cone is not within the optimal working range, then at step 315, the direction and distance the detectable position must be adjusted to be within the optimal working range may be determined.

At step 320, whether the detectable position of the suction cone may be maintained within the optimal working range by only adjusting the suction cone may be determined. If the detectable position of the suction cone may be maintained by only moving the suction cone, then at step 325, a control signal may be generated, the control signal operable to adjust the position of the suction cone in the direction and distance determined in step 315. At step 350, whether manual confirmation is required to perform the adjustment may be determined. If no manual confirmation is required, then at step 355, automated adjustment of the suction cone may be performed, such that the detectable position of the suction cone is maintained within the optimal working range. If at step 350, manual confirmation is required, then at step 360, whether manual confirmation has been input may be determined. If manual confirmation has not been input, then at step 365, the process may proceed to a standby mode until manual confirmation is input. If at step 350, manual confirmation is required, and at step 360, manual confirmation is determined to have been input, then at step 355, automated adjustment of the suction cone may be performed, such that the detectable position of the suction cone is maintained within the optimal working range.

In contrast, if at step 320, the detectable position of the suction cone may not be maintained within the optimal working range by only moving the suction cone, then at step 330, whether the detectable position may be maintained within the optimal working range by only moving a support alone, or in addition to the suction cone, may be determined. If neither the support alone, or in addition to the suction cone may be adjusted to maintain the suction cone within the optimal working range, then at step 331, a warning may be generated, the warning indicating that automated adjustment is unavailable. At step 332, the warning may be transmitted to a display to be presented to a user. The display may include multiple displays and may be a screen, a heads-up display, or a combination. Such warning, for example, may be in the form of a colored light, a blinking light, a flashing light, a sound, an alarm, a whistle, a graphic, or any other signal operable to indicate to the user that automated adjustment is not available to achieve maintenance of the suction cone within the optimal working range. The warning may be presented to the user in real time, preferably as soon as it is determined that automated adjustment is unavailable. Real time may mean in less than half a second, in less than one second, or otherwise in less than the normal reaction time of a user based on visual or acoustic information. After the warning is transmitted at step 332, the process terminates, as shown at step 311.

However, if at step 330, it is determined that the detectable position may be maintained within the optimal working range by moving the support alone, or in addition to the suction cone, then at step 335, a control signal may be generated, the control signal being operable to adjust the detectable position of the support (and the suction cone if necessary) in the direction and distance determined in step 315. At step 350, whether manual confirmation is required to perform the adjustment based on the generated control signal may be determined. If no manual confirmation is required, then at step 355, automated adjustment of the support (and the suction cone, if necessary) may be performed, such that the detectable position of the suction cone is maintained within the optimal working range. If at step 350, manual confirmation is required, then at step 360, whether manual confirmation has been input may be determined. If manual confirmation has not been input, then at step 365, the process may proceed to a standby mode until manual confirmation is input. If at step 350, manual confirmation is required, and at step 360, manual confirmation is determined to have been input, then at step 355, automated adjustment may be performed, such that the detectable position of the suction cone is maintained within the optimal working range. By maintaining the detectable position of the suction cone within the optimal working range, method 300 maintains a stable vacuum pressure between the eye, the docked suction ring, and the docked suction cone with no leakage.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A system for maintaining the position of a suction cone on an eye during laser ophthalmic surgery comprising:
a suction cone;
a first control device operable to adjust a position of the suction cone;
a measuring device operable to detect a detectable position of the suction cone and generate data relating to the detectable position;
a patient support;
a second control device operable to adjust a position of the patient support;
a display; and
a processor configured to:
receive data from the measuring device relating to the detectable position;
determine whether the detectable position of the suction cone is within an optimal working range;
determine a distance and direction the suction cone or patient support must be adjusted to maintain the detectable position within the optimal working range;
determine whether only the suction cone can be adjusted to maintain the detectable position within the optimal working range, and if not, whether the patient support may be adjusted alone or in addition to the suction cone;
generate a control signal operable to adjust the position of the suction cone, if only the suction cone may be adjusted;
generate a control signal operable to adjust a position of the patient support, if only the patient support may be adjusted;
generate a first control signal operable to adjust the position of the suction cone and a second control signal operable to adjust a position of the patient support, if neither the suction cone or the patient support may be adjusted alone;
transmit the first and second control signals to maintain the detectable position within the optimal working range, wherein the optimal working range is a range in a Z-direction that is preferable or necessary for the suction cone to be docked within, where suction between the eye, a docked suction ring, and the docked suction cone is stable;
process the data relating to the detectable position to generate a pictorial representation of the suction cone and the eye; and
transmit the pictorial representation to the display.

2. The system of claim 1, wherein the measuring device is operable to detect a detectable position of the suction cone by using light barriers.

3. The system of claim 1, wherein the measuring device is operable to detect a detectable position of the suction cone by using switches.

4. The system of claim 1, wherein the measuring device is operable to detect a detectable position of the suction cone by using an eye camera or multiple eye cameras.

5. The system of claim 1, wherein the measuring device is operable to detect a detectable position of the suction cone by using an eye tracking system.

6. The system of claim 1, wherein the patient support is a couch.

7. The system of claim 1, wherein the patient support is a bed.

8. The system of claim 1, further comprising a device for manual confirmation of an adjustment, the device operable to input a confirmation.

9. The system of claim 8, wherein the device for manual confirmation of an adjustment is a button, a switch, a key, a joystick, a receiver for a spoken confirmation, or any combination thereof.

10. The system of claim 8, wherein the processor is further configured to require receipt of a manual confirmation input before either generating a control signal or transmitting a control signal already generated.

11. A method for maintaining the position of a suction cone on an eye during laser ophthalmic surgery comprising:
providing a processor configured to:
receive data from a measuring device relating to a detectable position of a suction cone;
determine whether the detectable position of the suction cone is within an optimal working range;
determine a distance and direction the suction cone or a patient support must be adjusted to maintain the detectable position within the optimal working range;
determine whether only the suction cone can be adjusted to maintain the detectable position within the optimal working range, and if not, whether the patient support may be adjusted alone or in addition to the suction cone;
generate a control signal operable to adjust the position of the suction cone, if only the suction cone may be adjusted;
generate a control signal operable to adjust a position of the patient support, if only the patient support may be adjusted;
generate a first control signal operable to adjust the position of the suction cone and a second control signal operable to adjust a position of the patient support, if neither the suction cone or the patient support may be adjusted alone;
transmit the first and second control signals to maintain the detectable position within the optimal working range, wherein the optimal working range is a range in a Z-direction that is preferable or necessary for the suction cone to be docked within, where suction between the eye, a docked suction ring, and the docked suction cone is stable;
process the data relating to the detectable position to generate a pictorial representation of the suction cone and the eye; and
transmit the pictorial representation to a display.

12. The method of claim 11, wherein the measuring device is operable to detect a detectable position of the suction cone by using light barriers.

13. The method of claim 11, wherein the measuring device is operable to detect a detectable position of the suction cone by using switches.

14. The method of claim 11, wherein the measuring device is operable to detect a detectable position of the suction cone by using an eye camera or multiple eye cameras.

15. The method of claim 11, wherein the measuring device is operable to detect a detectable position of the suction cone by using an eye tracking system.

16. The method of claim 11, wherein the patient support is a couch.

17. The method of claim 11, wherein the patient support is a bed.

18. The method of claim 11, further comprising determining whether manual confirmation is required to perform an adjustment of the suction cone or the patient support.

19. The method of claim 18, further comprising determining whether manual confirmation has been input.

20. The method of claim 19, wherein receipt of a manual confirmation input is required before a control signal is generated or a control signal already generated is transmitted.

* * * * *

UNITED STATES PATENT AND TRADEMARK OFFICE
CERTIFICATE OF CORRECTION

| | |
|---|---|
| PATENT NO. | : 11,376,159 B2 |
| APPLICATION NO. | : 16/334594 |
| DATED | : July 5, 2022 |
| INVENTOR(S) | : Michael Wittnebel and Mario Abraham |

It is certified that error appears in the above-identified patent and that said Letters Patent is hereby corrected as shown below:

On the Title Page

Item (71) "Applicant: Novartis AG, Basel (CH)" should read:
--Alcon Inc., Fribourg (CH)--

Signed and Sealed this
Twenty-fifth Day of October, 2022

Katherine Kelly Vidal
*Director of the United States Patent and Trademark Office*